(12) United States Patent
Larsen (10) Patent No.: US 9,008,764 B2
(45) Date of Patent: Apr. 14, 2015

(54) DETERMINATION OF POSITION OF INJECTION NEEDLE

(75) Inventor: André Larsen, Dragør (DK)

(73) Assignee: Novo Nordisk A/S, Bagsvaerd (DK)

( * ) Notice: Subject to any disclaimer, the term of this patent is extended or adjusted under 35 U.S.C. 154(b) by 913 days.

(21) Appl. No.: 12/293,250

(22) PCT Filed: Mar. 20, 2007

(86) PCT No.: PCT/EP2007/052633
§ 371 (c)(1),
(2), (4) Date: Oct. 13, 2008

(87) PCT Pub. No.: WO2007/107561
PCT Pub. Date: Sep. 27, 2007

(65) Prior Publication Data
US 2009/0088662 A1   Apr. 2, 2009

Related U.S. Application Data

(60) Provisional application No. 60/791,067, filed on Apr. 11, 2006.

(30) Foreign Application Priority Data

Mar. 20, 2006   (EP) .................................... 06005599

(51) Int. Cl.
*A61B 5/05* (2006.01)
*A61M 5/42* (2006.01)
(Continued)

(52) U.S. Cl.
CPC .......... *A61M 5/427* (2013.01); *A61M 5/14248* (2013.01); *A61M 5/16836* (2013.01); *A61M 5/3129* (2013.01); *A61M 5/46* (2013.01); *A61N 1/08* (2013.01)

(58) Field of Classification Search
USPC ............................................. 600/547; 604/67
See application file for complete search history.

(56) References Cited

U.S. PATENT DOCUMENTS

| 3,944,843 A | 3/1976 | Vaz Martins |
| 4,871,351 A | 10/1989 | Feingold |

(Continued)

FOREIGN PATENT DOCUMENTS

| DE | 3236374 | 4/1984 |
| DE | 3923079 | 1/1991 |

(Continued)

OTHER PUBLICATIONS

Search Report issued in connection with counterpart European Application No. 06005599.3, mailed Oct. 4, 2006.

(Continued)

*Primary Examiner* — Max Hindenburg
*Assistant Examiner* — Renee Danega
(74) *Attorney, Agent, or Firm* — Wesley A. Nicolas; Reza Green; Richard W. Bork (57) ABSTRACT

The present invention relates to a method for detecting contact between an injection needle of a medication delivery device and a body of a patient. The method comprises the step of generating a contact signal in response to closure of an electrical signal path comprising an exterior surface part of the injection needle, an exterior surface part of a handle of the medication delivery device and at least part of the body of the patient. The present invention further relates to a method for determining the position of insertion of the injection needle, and to the insertion depth of the injection needle.

26 Claims, 11 Drawing Sheets

(51) Int. Cl.
*A61M 5/168* (2006.01)
*A61M 5/46* (2006.01)
*A61M 5/142* (2006.01)
*A61M 5/31* (2006.01)
*A61N 1/08* (2006.01)

(56) References Cited

U.S. PATENT DOCUMENTS

| | | | |
|---|---|---|---|
| 4,950,246 A | 8/1990 | Muller | |
| 5,135,485 A | 8/1992 | Cohen et al. | |
| 5,611,784 A * | 3/1997 | Barresi et al. | 604/211 |
| 5,628,309 A | 5/1997 | Brown | |
| 5,720,733 A | 2/1998 | Brown | |
| 5,741,211 A | 4/1998 | Renirie et al. | |
| 5,820,602 A | 10/1998 | Kovelman et al. | |
| 5,879,360 A | 3/1999 | Crankshaw | |
| 5,879,630 A | 3/1999 | Lescouzeres et al. | |
| 5,928,201 A | 7/1999 | Poulsen et al. | |
| 5,933,671 A | 8/1999 | Stephany et al. | |
| 5,954,700 A | 9/1999 | Kovelman | |
| 5,971,963 A | 10/1999 | Choi | |
| 5,989,221 A | 11/1999 | Hjertman | |
| 6,019,745 A | 2/2000 | Gray | |
| 6,110,148 A | 8/2000 | Brown et al. | |
| 6,161,364 A | 12/2000 | Kolberg | |
| 6,391,005 B1 * | 5/2002 | Lum et al. | 604/117 |
| 6,547,755 B1 * | 4/2003 | Himbert et al. | 604/67 |
| 2001/0034506 A1 | 10/2001 | Hirschman et al. | |
| 2002/0002326 A1 * | 1/2002 | Causey et al. | 600/300 |
| 2002/0020654 A1 | 2/2002 | Eilersen | |
| 2004/0010204 A1 * | 1/2004 | Weber et al. | 600/547 |
| 2004/0158304 A1 | 8/2004 | Cory et al. | |
| 2005/0251120 A1 * | 11/2005 | Anderson et al. | 606/20 |
| 2006/0118612 A1 | 6/2006 | Christoffersen et al. | |

FOREIGN PATENT DOCUMENTS

| | | |
|---|---|---|
| EP | 017318 | 10/1980 |
| EP | 422482 | 4/1991 |
| EP | 454331 | 10/1991 |
| EP | 615762 | 9/1994 |
| EP | 1074273 | 2/2001 |
| EP | 1557163 | 7/2005 |
| FR | 2622457 | 5/1989 |
| GB | 2153445 | 8/1985 |
| GB | 2229497 | 9/1990 |
| GB | 2309644 | 8/1997 |
| IN | 165367 | 3/1986 |
| JP | 56083360 A | 7/1981 |
| JP | 09166474 | 6/1997 |
| JP | 2002028247 A | 1/2002 |
| JP | 2003159331 A | 6/2003 |
| WO | WO 85/02256 | 5/1985 |
| WO | WO 99/07425 | 2/1999 |
| WO | WO 00/37129 | 6/2000 |
| WO | WO 02/24257 * | 3/2002 |
| WO | WO 03/063680 | 8/2003 |
| WO | WO 97/33638 | 9/2003 |
| WO | WO 2004/080306 | 9/2004 |
| WO | WO 2004/084795 | 10/2004 |
| WO | 2005/084139 A2 | 9/2005 |
| WO | 2007107558 A2 | 9/2007 |
| WO | WO 2007/107558 | 9/2007 |

OTHER PUBLICATIONS

Search Report issued in connection with counterpart PCT Application No. PCT/EP2007/052633, mailed Feb. 20, 2008.

English Language Abstract of German Patent No. 3923079, published Jan. 24, 1991, obtained from espacenet.com database.

English Language Abstract of German Patent No. 3236374, published Apr. 5, 1984, obtained from espacenet.com database.

English Language Abstract of European Patent No. 422482, published Apr. 17, 1991, obtained from espacenet.com database.

English Language Abstract of Indian Patent No. 165367, published Mar. 20, 1986, obtained from espacenet.com database.

* cited by examiner

DETERMINATION OF POSITION OF INJECTION NEEDLE

CROSS-REFERENCE TO RELATED APPLICATIONS

This application is a 35 U.S.C. §371 national stage application of International Patent Application PCT/EP2007/052633 (published as WO 2007/107561), filed Mar. 20, 2007, which claimed priority of European Patent Application 06005599.3, filed Mar. 20, 2006; this application further claims priority under 35 U.S.C. §119 of U.S. Provisional Application 60/791,067, filed Apr. 11, 2006.

FIELD OF THE INVENTION

The present invention relates to a method for determining contact between an injection needle of a medication delivery device and the body of a patient. In particular, the present invention relates to a method for detecting when a closed electrical signal path comprising the injection needle, part of the body of the patient and the handle of the medication delivery device is established. The present invention further relates to a method for determining whether the injection needle has been inserted into non-muscular tissue, such as epidermis, dermis or subcutis tissue, or muscular tissue. The method distinguishes between muscular and non-muscular tissue by measuring an electrical parameter of the tissue in which the injection needle has been inserted.

BACKGROUND OF THE INVENTION

For users of medication delivery devices it may be difficult to determine when effective contact has been established between an injection needle and the body. Also, when using a medication delivery device it may be very difficult for the user of the device to determine the exact position of the tip of the injection needle in the body—i.e. whether the injection needle by accident has entered a vein or entered muscular tissue.

WO 02/060325 discloses an apparatus for non-invasive determination of the allowable penetration depth of an injection needle when injecting into the subcutis layer of the human body. The apparatus comprises an elongated housing with an ultrasonic measuring head for transmitting an ultrasonic signal into the human body and receiving a reflected signal reflecting from the muscle membrane separating the muscular tissue from the subcutis tissue. The apparatus includes an electronic circuit for analysing the ultrasonic signals and calculating the possible allowable penetration depth of the injection needle in order to avoid penetration of the muscle membrane. The allowable penetration depth of the injection needle is instantly shown in a display integrated in the housing in the format as the allowable standard needle sizes recommended for that particular anatomical injection site. It is a disadvantage of the apparatus shown in WO 02/060325 that it needs to be removed and replaced with a medication delivery device before the actual dose of medicament can be injected into the body. This replacement introduces the risk that the medication delivery device is not positioned at exactly the same spot as the apparatus suggested in WO 02/060325. If the positioning of the two apparatuses is not exactly the same the medication delivery device may be positioned at a position where the allowable penetration depth differs from what has been measured with the apparatus according to WO 02/060325.

U.S. Pat. No. 2,763,935 discloses an early arrangement for measuring the thickness of outer fat layers on bodies of humans or swine. According to the arrangements suggested in U.S. Pat. No. 2,763,935 one or more electrodes are inserted into the fat layer whereby electrical parameters of the fat layer are measurable. U.S. Pat. No. 6,391,005 relates to similar but newer arrangement for measuring the penetration depth into an object.

WO 03/092487 relates to a doser comprising a syringe with an injection needle which extends beyond the doser itself. The doser comprises an engagement face in the vicinity of the injection needle so that the engagement face rests against the surface of the tissue into which the injection needle is inserted during expelling of a set dose of medication. Detector means are provided on the engagement face to sample signals on the skin of the patient. In WO 03/092487 the detector means involves a sensor for sensing heart beat signals. Thus, when heart beat signals are detectable the engagement face abuts the surface of the tissue and the injection needle is inserted in the patient. It is a disadvantage of the arrangement suggested in WO 03/092487 that additional and specific sensors are required in order to determine whether contact to with skin has been established.

FR 2 622 457 A discloses a microprocessor-controlled device for administering or sampling liquid products as well as micro currents. The device comprises a syringe fitted with an injection needle. An electronic micro circuit controls the operation of an electric motor which actuates a rack which ensures penetration and retraction of the injection needle. The micro circuit further controls an electric motor which drives a rack actuating a piston. The device suggested in FR 2 622 457 A is particularly intended for use within mesotherapy. In one embodiment suggested in FIG. 4 of FR 2 622 457 A an external electrode is electrically connected to the device via a cable. This external electrode is adapted to be held by the patient to receive an injection. By measuring the conductivity between the injection needle and the external electrode the position of injection is determinable. The device suggested in FR 2 622 457 A is a rather bulky device. In addition, the electrode used for determining the position of injection is an external electrode. By applying an external electrode the device suggested in FR 2 622 457 A becomes even more bulky and less user friendly.

It is an object of the present invention to provide a simpler arrangement for determining when contact between injection needle and the body of the patient has been established. By simpler is meant that no additional sensors are required.

It is a further object of the present invention to provide a method for determining whether the injection needle has entered for example epidermis, dermis or muscular tissue. Injection into for example muscular tissue should be avoided since a medicament, such as insulin, injected into muscular tissue is absorbed much faster compared to a medicament injected into for example subcutis tissue.

To comply with the above objects, the present invention suggests a method for measuring an electrical parameter, such as the impedance, of a closed electrical signal path including the body of the patient using the medication delivery device.

It is an advantage of the present invention that an insertion of an injection needle into the body of a patient can be detected by simply measuring an electrical parameter of the closed electrical signal path. No additional equipment, except some basic electronics, is required in order to perform this measurement.

Furthermore, it is an advantage of the present invention that changes in human tissue may be monitored as the injection needle enters the body. Thus, it is possible to distinguish whether the injection needle is in non-muscular tissue, such as epidermis, dermis or subcutis, only, or whether the injection needle has entered a region being dominated by muscular tissue.

SUMMARY OF THE INVENTION

The above-mentioned objects are complied with by providing, in a first aspect, a medication delivery device comprising

- a needle receiving portion adapted to receive an injection needle having an electrically conducting exterior surface part, the needle receiving portion being adapted to galvanically or capacitively connect to the electrically conducting exterior surface part of the injection needle,
- an electrically conducting exterior surface part forming part of a handle of the medication delivery device, the electrically conducting exterior surface part of the handle forming an integral part of the medication delivery device, and
- a sensing arrangement arranged between the needle receiving portion and the electrically conducting exterior surface part forming part of the handle.

The term "handle" is to be interpreted broadly. Thus, any exterior surface part of the medication delivery device that is galvanically separated from the injection needle, when the injection needle is mounted on the medication delivery device, may, in principle, be regarded as a handle as long as said exterior surface part of the medication delivery device is adapted to be gripped on or touched by the hand of a user. Thus, the exterior surface part forming the handle may be a part of a housing of the medication delivery device. Alternatively, the handle may be a user operable actuator, such as a push button, disposed in or on the housing.

By capacitively connect is meant that the needle receiving portion may couple capacitively to the electrically conducting exterior surface part of the injection needle via a medicament in a medicament containing cartridge. Thus, the needle receiving portion may couple capacitively to a back end of the injection needle, said back end of the injection needle entering the cartridge via a pierceable septum at the cartridge neck.

The sensing arrangement may comprise an electrical circuit, for example implemented as an ASIC, adapted to measure an impedance value of an object closing an exterior signal path between the electrically conducting surface part of the injection needle galvanically connected to needle receiving portion and the electrically conducting exterior surface part forming part of the handle.

The medication delivery device may further comprise signaling means adapted to provide a signal to a user of the medication delivery device in response to a measured impedance value. The signaling means may comprise acoustical signaling means and/or visual signaling means.

The medication delivery device may further comprise an electrical circuit for generating and providing a time varying electric signal to the needle receiving portion or to the electrically conducting exterior surface part forming part of the handle. The time varying electrical signal may have a frequency of at least 5 kHz, such as at least 50 kHz, such as at least 100 kHz whereas the time varying electrical signal may have an amplitude value in the range 50-500 mV, such as in the range 75-250 mV, such as in the range 100-200 mV, such as approximately 150 mV.

The needle receiving portion may, preferably, be adapted to detachably retain the injection needle in a fixed position relative to the medication delivery device.

In a second aspect, the present invention relates to a medication delivery device adapted to determine the type of tissue into which a tip of an injection needle of the medication delivery device has been inserted, the medication delivery device comprising

- means for determining a value of an electrical signal of a closed electrical signal path comprising an exterior surface part of the injection needle, an exterior surface part of a handle of the medication delivery device and at least part of the body of the patient, the exterior surface part of the handle forming an integral part of the medication delivery device,
- means for determining which of a number of predetermined ranges of values the determined value falls within, and
- means for generating an information signal to the user of the medication delivery device in accordance therewith.

Again, the term "handle" is to be interpreted broadly. Thus, any exterior surface part of the medication delivery device that is galvanically separated from the injection needle, when the injection needle is mounted on the medication delivery device, may, in principle, be regarded as a handle as long as said exterior surface part of the medication delivery device is adapted to be gripped on or touched by the hand of a user. Thus, the exterior surface part forming the handle may be a part of a housing of the medication delivery device. Alternatively, the handle may be a user operable actuator, such as a push button, disposed in or on the housing.

The generated information signal may comprise an alarm signal, the alarm signal being generated if the determined value falls within a predetermined range of values associated with the tip of the injection needle being inserted into for example muscular tissue. Contrary, the generated information signal may comprise a clearing signal, the clearance signal being generated if the determined value falls within a predetermined range of values associated with the tip of the injection needle being inserted into for example subcutis tissue. A clearance signal may also be generated if the tip of the injection needle is inserted into other types of allowable tissues.

The number of predetermined ranges of values may comprise a first, a second and a third predetermined range, wherein the first predetermined range comprises expected values associated with a first area of injection on the body, and wherein the second predetermined range comprises expected values associated with a second area of injection on the body, and wherein the third predetermined range comprises expected values associated with a third area of injection on the body. The first, the second and the third area of injection on the body may be associated with the thigh, the stomach and a buttock, respectively. However, other areas may also be relevant.

The determined value of the electrical signal may comprise an amplitude value of a time varying electrical signal having a frequency of least 5 kHz, such as at least 50 kHz, such as at least 100 kHz. However, other electrical parameters like for example phase or impedance are also a measurable value. The time varying signal may comprise a plurality of time varying signals of different frequencies.

The medication delivery device according to the first and second aspects may be a handheld pen-shaped medication delivery device. Alternatively, the medication delivery device may be an infusion pump in form of a patch adapted to be attached to the skin of the patient. In case of the latter, the handle may be in the form of a surface opposing the surface of the patch abutting the skin of the patient.

In a third aspect, the present invention relates to a method for determining the type of tissue into which a tip of an injection needle of a medication delivery device has been inserted, the method comprising the steps of inserting the injection needle of the medication delivery device into the body tissue, determining a value of an electrical signal of a closed electrical signal path comprising an exterior surface part of the injection needle, an exterior surface part of a handle of the medication delivery device and at least part of the body of the patient, the exterior surface part of the handle forming an integral part of the medication delivery device, determining which of a number of predetermined ranges of values the determined value falls within, and generating an information signal to the user of the medication delivery device in accordance therewith.

Again, the term "handle" is to be interpreted broadly as mentioned in connection with the first and second aspects of the present invention. Also, the considerations regarding the generated information signal, the predetermined ranges of values, the signaling means and the characteristics of the electrical signal are similar to what is mentioned in connection with the first and second aspect of the present invention.

In a fourth aspect, the present invention relates to a method for detecting contact between an injection needle of a medication delivery device and a body of a patient, the method comprising the step of generating a contact signal in response to closure of an electrical signal path comprising an exterior surface part of the injection needle, an exterior surface part of an integrated handle of the medication delivery device and at least part of the body of the patient.

The contact signal may be generated in response to a measurement of a value of an electrical signal of the electrical signal path comprising the exterior surface part of the injection needle, the exterior surface part of the integrated handle of the medication delivery device and at least part of the body of the patient.

The measured value of the electrical signal may comprise an amplitude, phase or impedance value of the electrical signal, said value being measured in response to applying a time varying electrical signal to the injection needle. The time varying electrical signal may have a frequency of at least 5 kHz, such as at least 50 kHz, such as at least 100 kHz, and an amplitude value in the range 50-500 mV, such as in the range 75-250 mV, such as in the range 100-200 mV, such as approximately 150 mV.

Alternatively, contact between the injection needle and the skin of the body may also be detected using a capacitive load principle.

BRIEF DESCRIPTION OF THE DRAWINGS

The present invention will now be explained with reference to the accompanying figures in that FIG. 1 shows the general aspect of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to a method for establishing a closed electrical signal path, i.e. a closed loop, including the injection needle, the needle mount, the housing of the medication delivery device and the body of the user of the medication delivery device. An electronic circuit capable of inducing a current flow in the loop is arranged within the housing of the medication delivery device. When a current of a predetermined level flows in this closed signal path the needle of the medication delivery device has at least partly entered into the body of the user of the medication delivery device in that insertion of the injection needle into the body closes the loop whereby a detectable current is allowed to flow. In fact, a current is allowed to flow in the closed signal path as soon as the injection needle is in contact with the skin of the body. The fact that a current is allowed to flow is a consequence of an impedance change in that the impedance, before the injection needle enters the body or comes in contact with the skin of the body, is essentially infinity whereas the impedance of the closed loop has a finite and thereby significantly lower value.

To signal to the user of the medication delivery device that the needle of the medication delivery device has either entered the body or is in contact with the skin an audible, visual or another type of contact signal is generated. Thus, when the user of the medication delivery device registers this contact signal he or she can be certain that the injection needle has entered his or hers body.

In order to establish the above-mentioned electrical signal path the medication delivery device provides an electrical connection between at least part of the outer surface of the injection needle and at least part of the outer surface of the medication delivery device—i.e. the surface to be in contact with the hand/fingers of the user of the medication delivery device. Obviously, the relevant outer surface parts of the medication delivery device and the injection needle need to be electrically conducting. The electrical connection between the injection needle and the outer surface of the medication delivery device includes an electrical connection across a hub in which the injection needle is mounted.

The concept of the present invention is also applicable in connection with monitoring injected doses of medicament from the medication delivery device. For example, if the injection of medicament from the medication delivery device is in somehow monitored, the knowledge of whether the needle was inserted into the body of the patient or not may be used to distinguish "real shots" from "air shots". Thus, a marker may be added to the injection information for real shots. In this way information relating to the accumulated amount of medication expelled from the medication delivery device and into the body is available.

The present invention also relates to a method for distinguishing whether the injection needle of a medication delivery device has entered non-muscular tissue, such as epidermis, dermis or subcutis tissue, only or whether the needle of the medication delivery device has at least partly been inserted into muscular tissue. Injection of for example insulin directly into muscular tissue can be dangerous for the patient because insulin injected into muscular tissue is absorbed significantly faster compared to insulin injection into subcutis tissue.

The method according to this aspect of the present invention can rely on a measuring of the impedance between the injection needle of the medication delivery device and at least part of an exterior surface of the medication delivery device. Other electrical parameters such as amplitude, phase etc. are also applicable measurable parameters. However, in the following the present invention will be described as if only impedance values of the closed signal path are detected. The present invention should however not be limited to impedance measurements only. The before-mentioned electrical parameters are equally applicable.

The signal path between the injection needle and the exterior surface of the medication delivery device includes the part of the body between the point of injection and the fingers holding the medication delivery device. Thus, the impedance of the body will depend on the type of tissue into which the injection needle has been inserted.

This tissue dependent impedance can be detected by electronic means by applying an alternating electrical signal to the injection needle and sweeping the frequency of this signal over a given range. Alternative, an alternating electrical signal having a fixed frequency can be applied. Even further, an alternating electrical signal being constituted by a plurality of signals of fixed frequencies can also be applied. The measured impedance of the body will depend on whether the injection needle has been inserted into non-muscular tissue or whether the needle has also been inserted into a muscle. As already mentioned it is expected that before the needle is inserted into the body of the patient the impedance between the injection needle and the outer surface of the medication delivery device is close to infinity because the signal path is not closed. When the injection needle comes into some sort of contact with the body the signal path is closed and an electrical current is allowed to flow in said closed signal path. When the injection needle enters the body the impedance will decrease to a certain value. This value is expected to further decrease when the needle enters a muscular structure in the body of the patient.

Thus, by constantly measuring the impedance of the closed signal path including the injection needle, an outer surface of the medication delivery device and the body of the patient information is provided whether the injection needle has entered muscular tissue or not. If the injection needle by accident enters muscular tissue this information can be logged in a control circuit positioned within the medication delivery device. Also, the measured impedance may be compared with a series of expected values in order to determine whether the injection needle is in epidermis, dermis, subcutis or muscular tissue. In addition, the principle behind the present invention may also be applied to detect whether an injection needle has accidentally been inserted into for example a vein.

Figure 1:
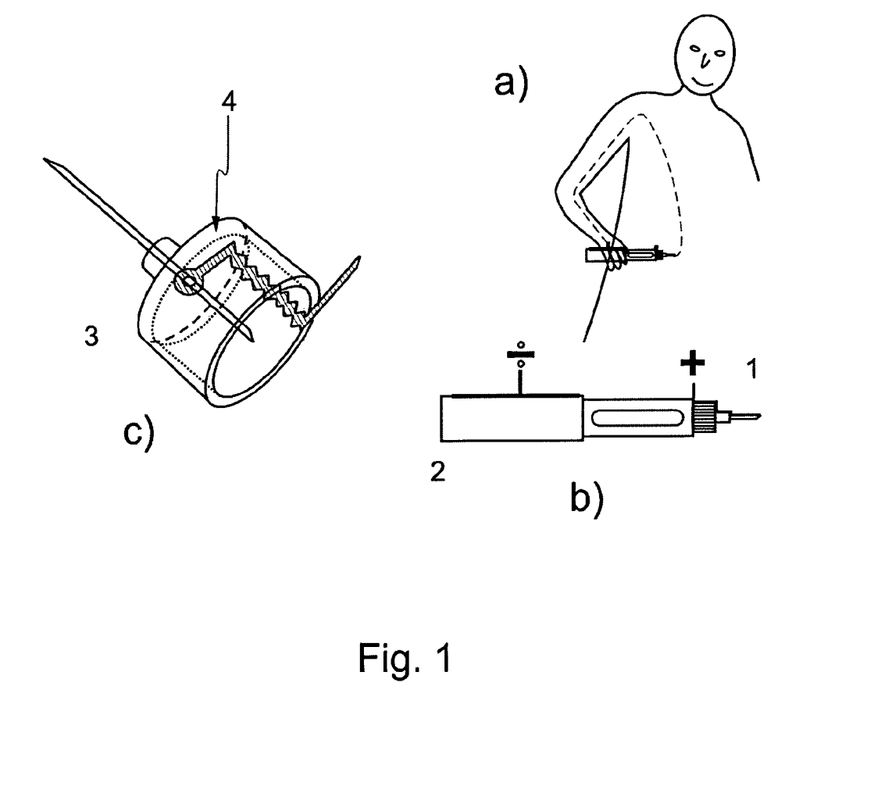

Referring now to FIG. 1 the general aspect of the present invention is depicted in FIG. 1a where a patient has inserted an injection needle of a medication delivery device into the stomach region. The medication delivery device may in principle be adapted to expel any kind of medication, such as for example insulin. The medication delivery device houses a medicament containing cartridge and some sort of mechanical expel mechanism adapted to move a piston in the cartridge so as to expel a set dose of medicament from the medication delivery device. The force necessary to move the piston in the cartridge can be applied by the patient only. Alternatively, some sort of resilient element, such as a linear spring or torsion spring, can assist the patient expelling medicament from the cartridge. In the first situation the device is a manual medication delivery device whereas in the latter situation the device is an automatic or servo medication delivery device. Finally, the present invention may also apply of motorized medication delivery devices.

As illustrated in FIG. 1a the medication delivery device and a part of the body of the patient form an electrical signal path in the moment the injection needle of the medication delivery device is inserted into the body of the patient. In fact a slight contact between the injection needle and the skin is sufficient to close the signal path. This closed signal path is indicated by the dashed line in FIG. 1a. In order for this closed signal path to be established the injection needle 1 and the handle 2 of the medication delivery device must be electrically connected—see FIG. 1b. An electronic circuit forms part of this connection in that appropriate signals need to be applied between the handle and the injection needle in order to determine an electrical parameter, such as the impedance, of the closed signal path. In addition, the mount or hub 3 in which the injection needle 1 is mounted is equipped with an integrated electrical connector 4 for providing an electrical connection across the mount or hub 3—see FIG. 1c. Alternatively, electrical connection to the injection needle may also be provided through the medicament and an electrically conducting piston and piston rod.

Figure 2:
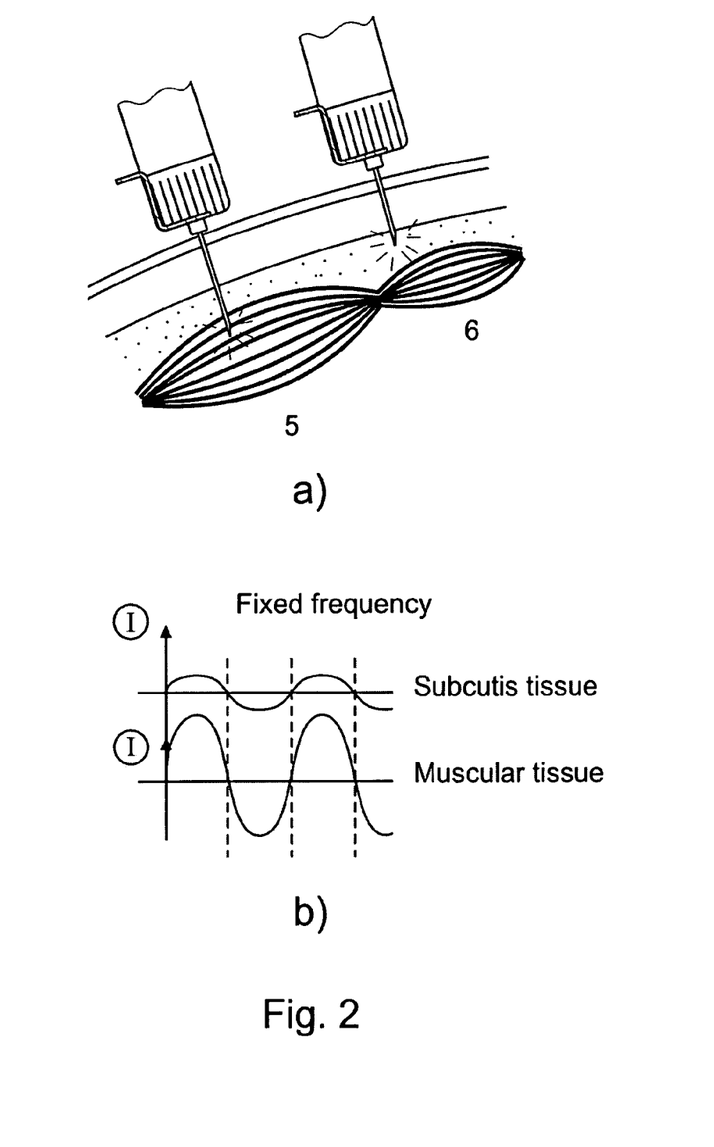
FIG. 2 illustrates how different types of tissues are distinguishable.

According to another embodiment of the present invention a method for distinguishing between different types of tissues is provided. According to this embodiment, now referring to FIG. 2, this method is capable for warning the patient in case the patient is about to expel a dose of medicament into a muscle, the epidermis or the dermis. As depicted in FIG. 2a an injection needle can accidentally be inserted into muscle 5, or it can correctly be inserted into the non-muscular (subcutis) region 6, the latter being the correct insertion. Looking from the skin-side of the patient it is difficult to determine whether the tip of the injection needle has accidentally entered a muscle. Since the muscular tissue is denser compared to non-muscular tissue the electrical impedance of muscular tissue is smaller than non-muscular tissue. Thus, by measuring the impedance of the body, and comparing the measured impedance with predetermined impedance values, it can be determined whether the injection needle has entered muscular tissue or not. Again, other electrical parameters than impedance are applicable—such measurable parameters may be amplitude, phase etc.

FIG. 2b depicts respond signals from the situations where the tip of the injection needle is non-muscular tissue (upper curve) and muscular tissue (lower curve). The signal applied to the closed signal path can be an alternating signal having a frequency of around 50 kHz.

Figure 3:
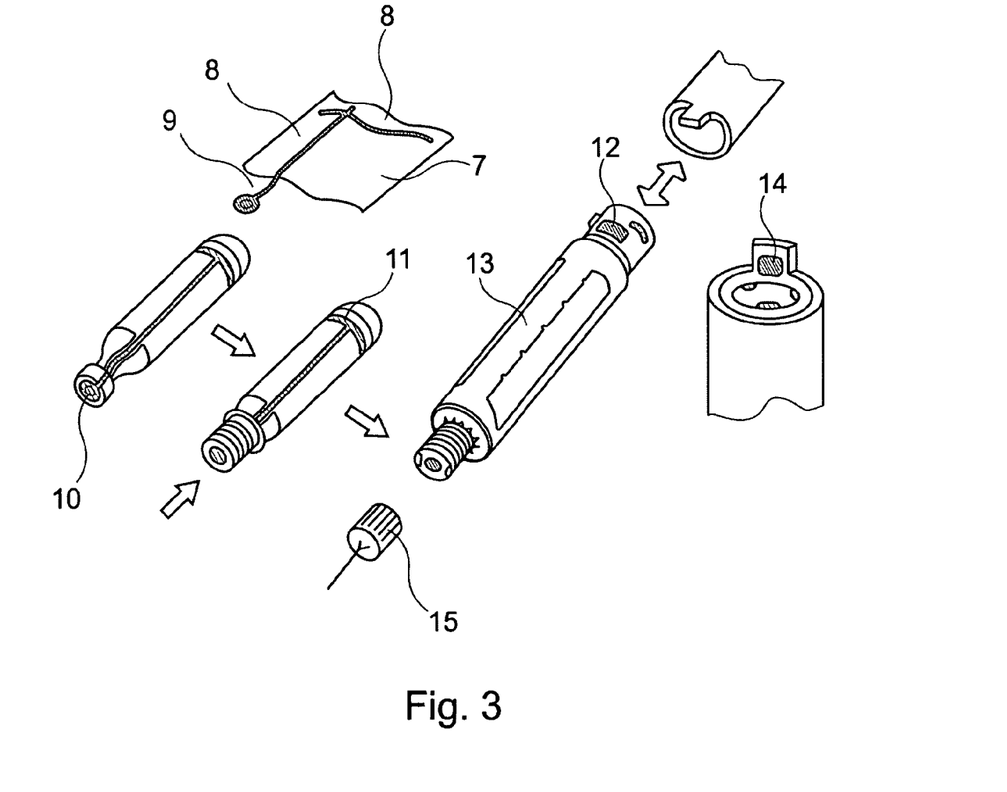
FIG. 3 shows a first way of establishing an electrical connection to the injection needle.

The injection needle can be electrically connected by various means. Referring now to FIG. 3, a label 7 with a conducting print 8 added on same side as the normal printed text is depicted. An extra strip 9 is attached to the normal shaped label with a shape fitting 10 on top of the cartridge septum under the code top. In the other end of the cartridge the shape of the label forms an electrically conducting ring 11 wrapped around the circular surface providing a contact all around the cartridge. A through-going hole 12 on the cartridge holder 13 just above the circular contact surface makes it feasible to establish an electrical connection between the cartridge label 7 and contacts 14 on an associated medication delivery device. The associated medication delivery device comprises an overhanging part including the contact set 14. This contact set 14 is electrically connected to a PCB inside the medication delivery device. An injection needle 15 is attached to the cartridge holder 13 so that a back end (not shown) of the injection needle penetrates the conducting part 10 of the label.

Figure 4:
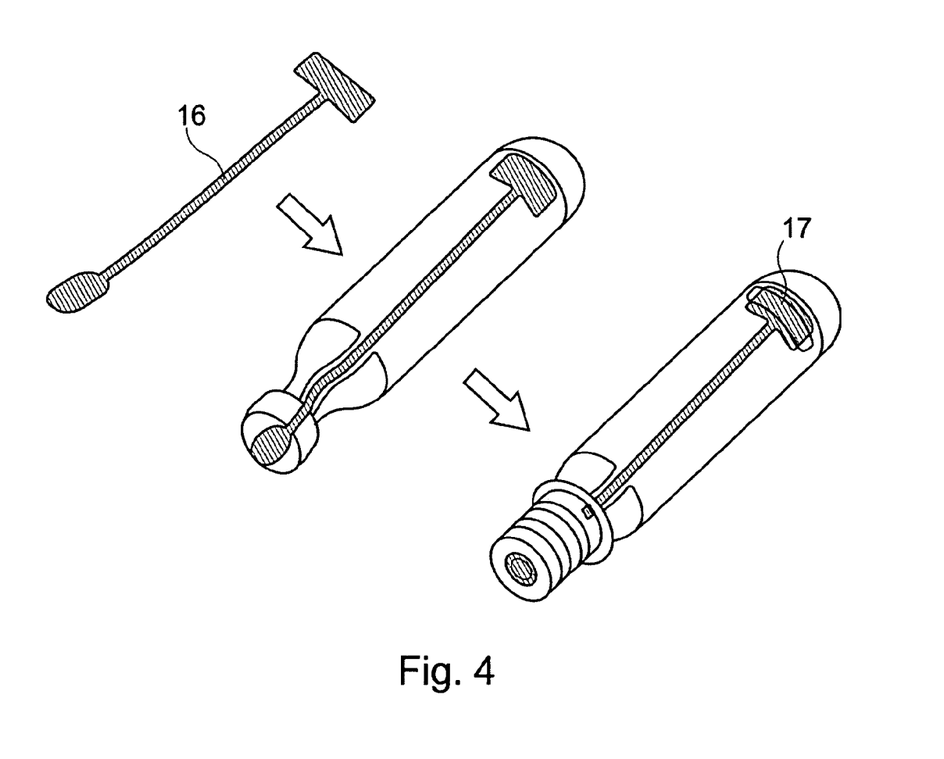
FIG. 4 shows a second way of establishing an electrical connection to the injection needle.

Alternatively, as depicted in FIG. 4, an ordinary label with a conducting metal foil 16 added under the label may be provided. A normal shaped label (44×53 mm) is attached to the cartridge. A hole 17 is punched in the label near the end of the cartridge so as to expose the metal foil 16. At the other end of the metal foil 16 the code top is attached on top of the foil between the code top and the septum. An injection needle (not shown) is attached to the cartridge holder so that a back end of the injection needle penetrates the conducting part of the label.

In FIGS. 3 and 4 the connection to the injection needle is provided by a galvanic connection in that a back end of the injection needle penetrates an electrode arranged across the septum of the cartridge. However, the connection to the injection needle can also be provided capacitively. By capacitively is meant that an electrode positioned near the cartridge neck (on the cartridge) or near the needle receiving portion of the cartridge holder couple capacitively to the electrically conducting exterior surface part of the injection needle via a medicament in the cartridge. Thus, it is possible to couple capacitively to the back end of the injection needle, said back end of the injection needle entering the cartridge via a pierceable septum at the cartridge neck.

Figure 5:
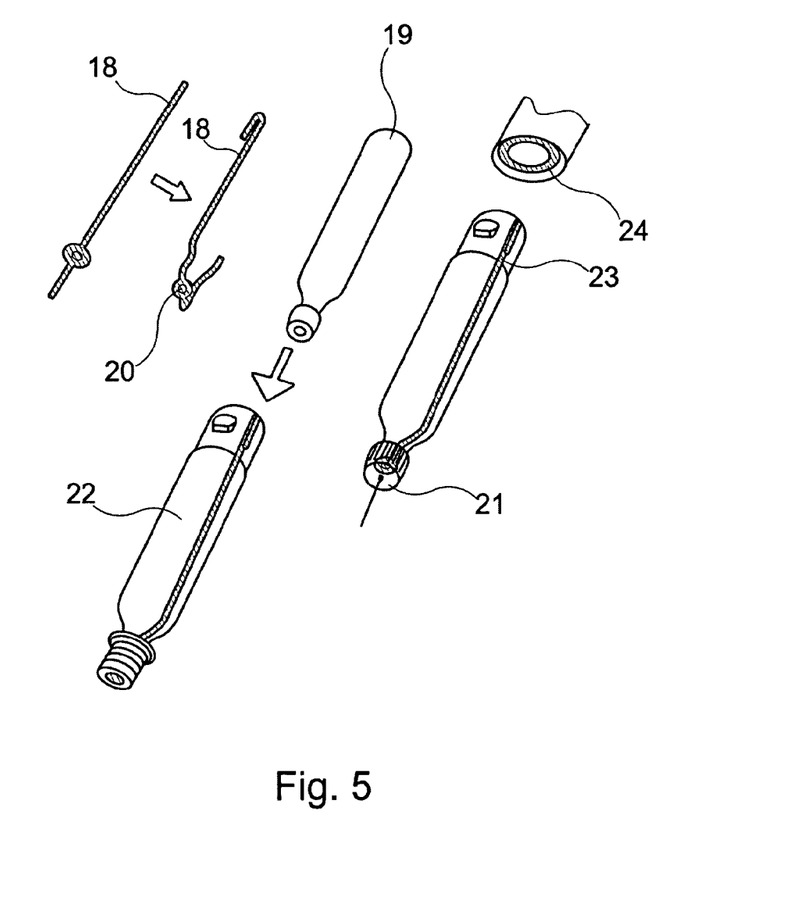
FIG. 5 shows a third way of establishing an electrical connection to the injection needle.

FIG. 5 shows a thin metal spring 18 wrapped around an ordinary cartridge 19 with an integrated contact 20 on top of the septum connecting direct to the back end of an injection needle 21. The metal spring 18 is mounted together with the cartridge and hidden inside the cartridge holder 22. Before use the contact area 20 is also acting as protection for the septum. In the rear end of the cartridge holder the metal spring 18 is glued and thereby fixed to the cylindrical surface 23. This contact is touching a connection ring 24 in the end of a medication delivery device thereby establishing an electrical connection between the two parts.

Figure 6:
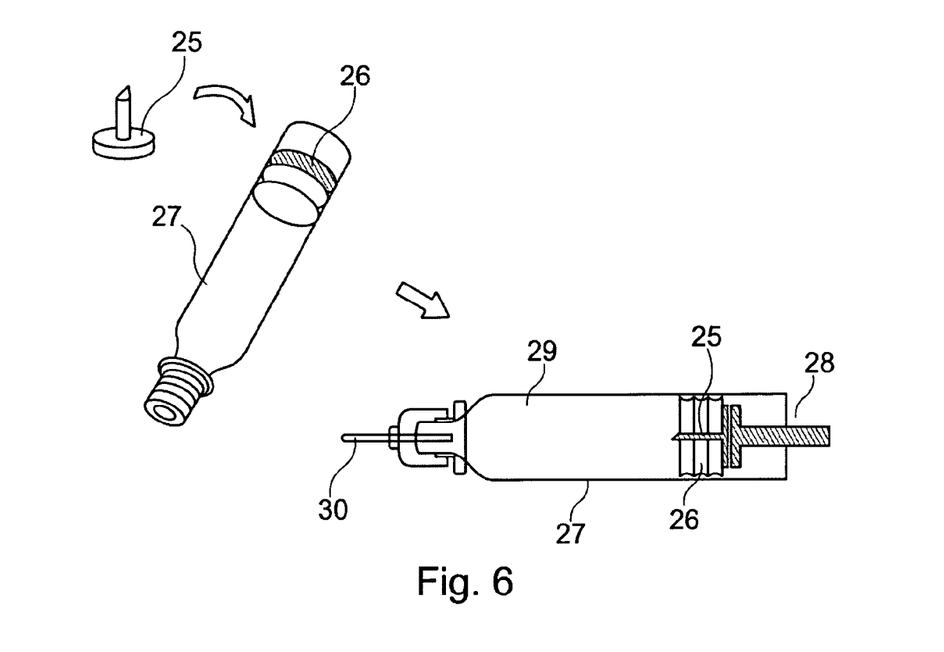
FIG. 6 shows a fourth way of establishing an electrical connection to the injection needle.

Referring now to FIG. 6, an electrical conducting plug 25 is integrated with or inserted into the plunger 26. When the cartridge 27 is positioned in a medication delivery device a piston rod 28 presses the plunger 26 to its starting position. Along with this, the plug 25 fully penetrates the plunger 26 whereby an electrical connection is established between the medicament 29 contained in the cartridge 27 and an outer portion of the plug 25. An electronic circuit of the medication delivery device is electrically connected to the piston rod 28 whereby an electrical connection is established to the injection needle 30 via the medicament 29 in the cartridge 27.

Figure 7:
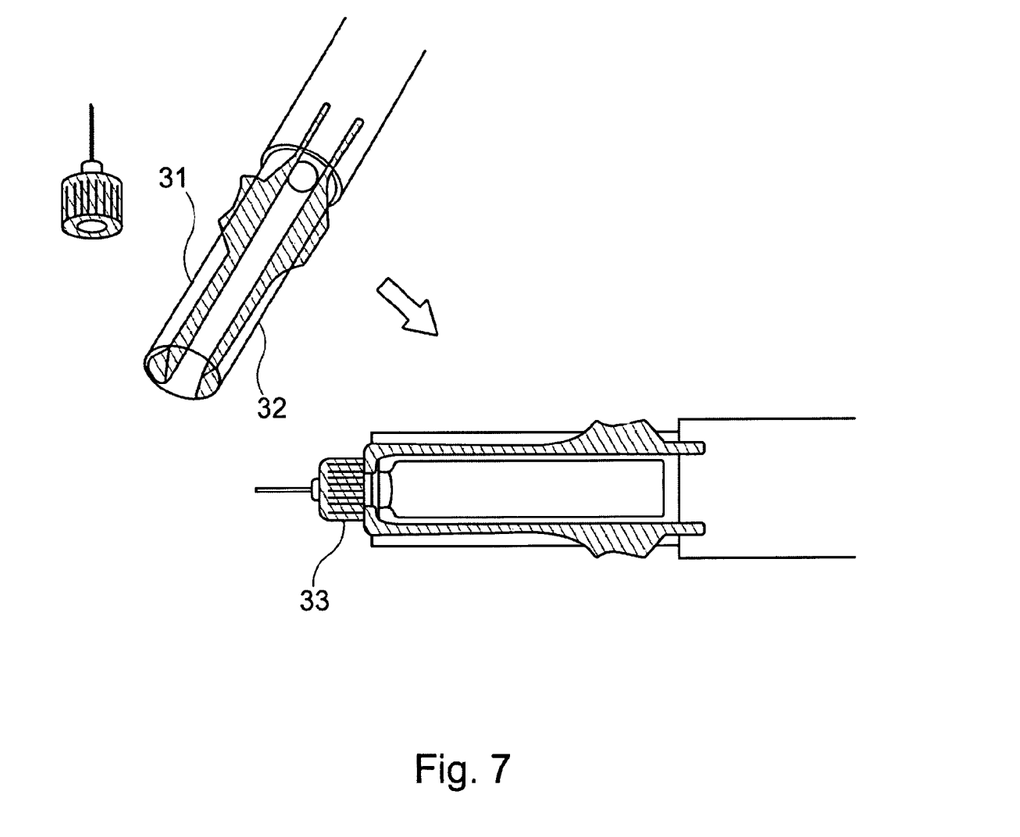
FIG. 7 shows a fifth way of establishing an electrical connection to the injection needle.

A medication delivery device with a special designed front loaded cartridge holder is shown in FIG. 7. The cartridge holder has two jaws 31, 32 keeping the cartridge in its correct position. The two jaws 31, 32 are electrically conducting and they have a built-in contact switch function. When an injection needle 33 is attached to the medication delivery device the needle contacts to the electronics of the device. Thus, the cartridge of the arrangement depicted in FIG. 7 needs no modification.

Figure 8:
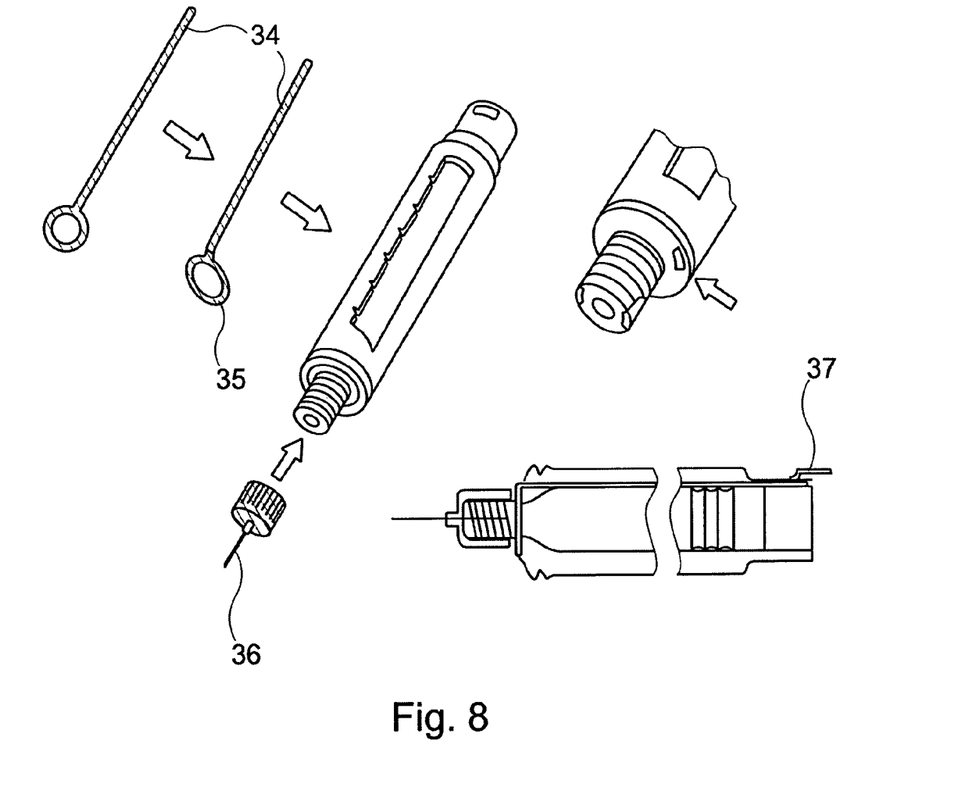
FIG. 8 shows a sixth way of establishing an electrical connection to the injection needle.

In FIG. 8, a metal spring 34 with a circular contact area 35 is depicted. The metal spring 34 is designed to fit standard cartridges. An injection needle 36 is attached to the device thereby establishing an electrical connection to the metal spring 34. The metal spring 34 has a wire connected to the end of the cartridge holder where a resilient contact set 37 connects to the electronics inside the medication delivery device.

Figure 9:
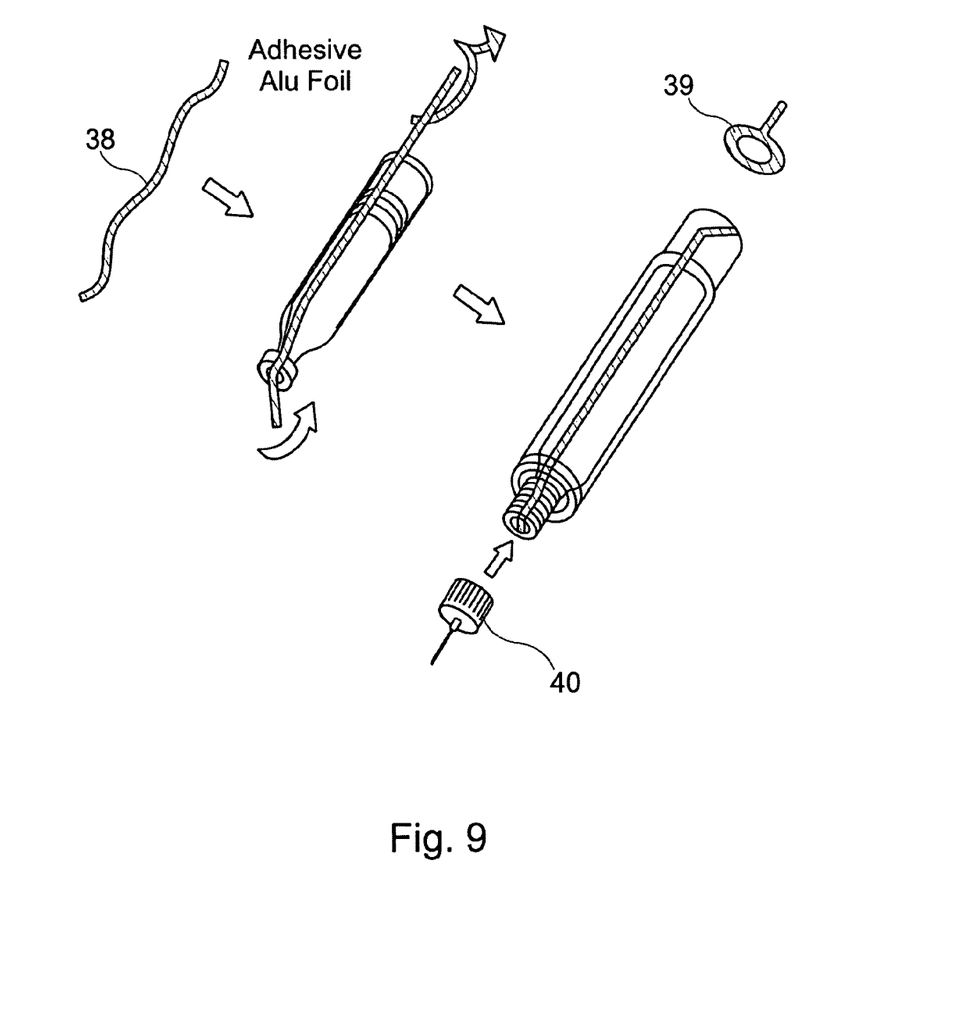
FIG. 9 shows a seventh way of establishing an electrical connection to the injection needle.

In FIG. 9 a conducting metal foil 38 with adhesive substance is attached on the cartridge. The metal foil extends in the full length of the cartridge and overhangs one end of the cartridge with about 15 mm. A ring shaped conducting steel element 39 connects the metal foil 38 to the electronics of the medication delivery device. An injection needle 40 is attached to the cartridge so that the back end (not shown) of the injection needle penetrates the metal foil attached to the cartridge.

Figure 10:
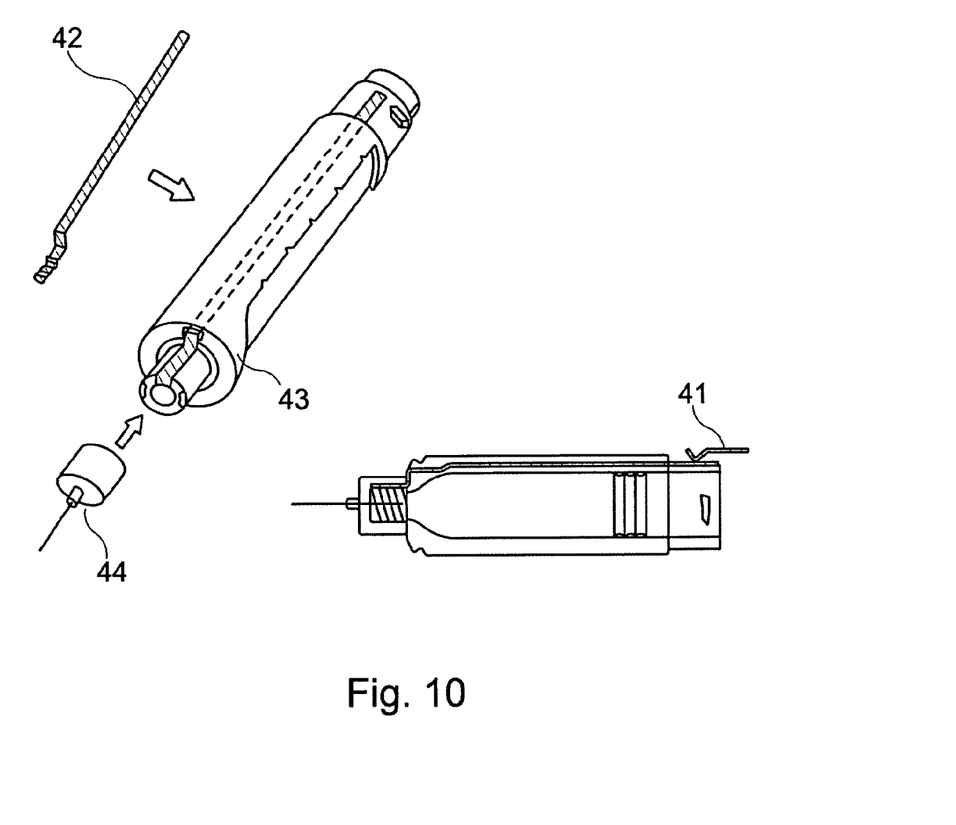
FIG. 10 shows an eighth way of establishing an electrical connection to the injection needle.

In FIG. 10 a metal spring 41 with a contact area provides electrical contact to a wire 42 attached to the cartridge 43. An injection needle 44 is attached to the medication delivery device whereby an electrical connection is provided between the metal spring 41 and the injection needle 44 via the wire 42. The metal spring 41 is in electrical connection with the electronics of the medication delivery device.

Figure 11:
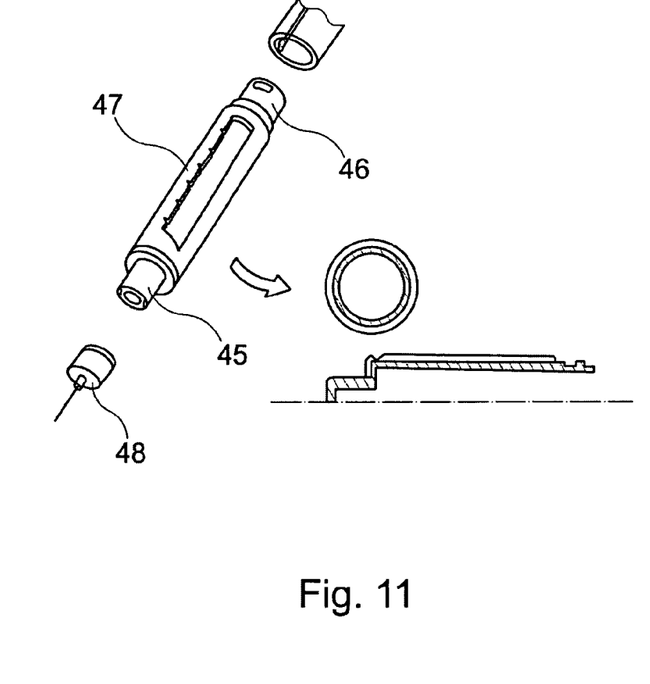
FIG. 11 shows a ninth way of establishing an electrical connection to the injection needle.

In FIG. 11 a cartridge holder is molded in a two component material where one material is an electrical isolator whereas the other material is an electrical conductor. In regions where electrical connections are to be established, e.g. at the injection needle end 45 and at the connection end 46, the electrically conducting material should be uncovered. At the cartridge holder body 47 the electrically isolating material covers the electrically conducting material. An injection needle 48 is connected to the cartridge holder.

Obviously, the determined impedance is dominated by the impedance of the body of the patient. One embodiment of the present invention relies on that the impedance of the body depends on the point of injection. Thus, if the patient chooses to insert the injection needle in the stomach region an impedance value within a certain impedance range is expected. However, if the patient chooses to insert the injection needle in the thigh an impedance value in a different impedance range is expected. Finally, if the patient chooses to insert the injection needle in a buttock an impedance value in a third impedance range is expected. Thus, since the measured impedance will fall within different regions depending on the position of injection, the position of injection can be logged and thereby saved in the medication delivery device, optionally with associated parameters, such as date and time of injection, amount of injected medicament, type of medicament etc. When the medicament containing cartridge is empty and needs to be replaced the before-mentioned logged information can be extracted from the medication delivery device and handled or processed by an external computer if necessary.

The invention claimed is:
1. A handheld pen-shaped medication delivery device for expelling a set dose of a medicament to a user, the handheld pen-shaped medication delivery device comprising:
  a housing,
  a needle mount for mounting an injection needle having an electrically conducting exterior surface part, the needle receiving portion being adapted to galvanically or capacitively connect to the electrically conducting exterior surface part of the injection needle, a handle being adapted to be gripped on or touched by the hand of the user, an electrically conducting exterior surface part forming part of the handle, the electrically conducting exterior surface part of the handle forming an integral part of the housing or an operable actuator disposed in or on the housing, an electrical circuit comprising:

structure for determining a value of an electrical signal of a closed electrical signal path comprising an electrically conductive exterior surface part of an injection needle mounted on the device, the electrically conducting exterior surface part of the handle and at least part of the body of the user, structure for determining which of a number of predetermined ranges of values the determined value falls within indicative of the type of tissue into which a tip of the injection needle mounted on the device has been inserted, and structure for generating an information signal to the user of the medication delivery device.

2. A medication delivery device according to claim 1, wherein the generated information signal comprises an alarm signal, the alarm signal being generated if the determined value falls within a predetermined range of values associated with the tip of the injection needle being inserted into muscular tissue.

3. A medication delivery device according to claim 2, wherein the medication delivery device comprises a log for saving the position of an injection.

4. A medication delivery device according to claim 1, wherein the generated information signal comprises a clearing signal, the clearance signal being generated if the determined value falls within a predetermined range of values associated with the tip of the injection needle being inserted into subcutis tissue.

5. A medication delivery device according to claim 4, wherein the medication delivery device comprises a log for saving the position of an injection.

6. A medication delivery device according to claim 1, wherein the number of predetermined ranges of values comprises a first, a second and a third predetermined range.

7. A medication delivery device according to claim 6, wherein the first predetermined range comprises expected values associated with a first area of injection on the body, and wherein the second predetermined range comprises expected values associated with a second area of injection on the body, and wherein the third predetermined range comprises expected values associated with a third area of injection on the body.

8. A medication delivery device according to claim 7, wherein the first, the second and the third area of injection on the body are associated with the thigh, the stomach and a buttock, respectively.

9. A medication delivery device according to claim 8, wherein the medication delivery device comprises a log for saving the position of an injection.

10. A medication delivery device according to claim 1, wherein the determined value of the electrical signal comprises an amplitude value of a time varying electrical signal.

11. A medication delivery device according to claim 10, wherein the frequency of the time varying signal is at least 5 kHz.

12. A medication delivery device according to claim 10, wherein the time varying signal comprises a plurality of time varying signals of different frequencies.

13. A medication delivery device according to claim 1, wherein the electric circuit is further adapted to measure an impedance value of an object closing an exterior signal path between the electrically conducting surface part of an injection needle galvanically connected to the needle receiving portion and the electrically conducting exterior surface part forming part of the handle for detecting whether or not the needle is inserted into the body of the user.

14. A medication delivery device according to claim 13, further comprising signaling structure adapted to provide a signal to a user of the medication delivery device in response to a measured impedance value.

15. A medication delivery device according to claim 14, wherein the signaling structure comprises acoustical signaling structure and/or visual signaling structure.

16. A medication delivery device according to claim 13, wherein the electrical circuit is adapted for generating and providing a time varying electric signal to the needle mount or to the electrically conducting exterior surface part forming part of the handle.

17. A medication delivery device according to claim 16, wherein the time varying electrical signal has a frequency of at least 5 kHz.

18. A medication delivery device according to claim 16, wherein the time varying electrical signal has a frequency of at least 50 kHz.

19. A medication delivery device according to claim 16, wherein the time varying electrical signal has a frequency of at least 100 kHz.

20. A medication delivery device according to claim 16, wherein the time varying electrical signal has an amplitude value in the range 50-500 mV.

21. A medication delivery device according to claim 16, wherein the time varying electrical signal has an amplitude value in the range 75-250 mV.

22. A medication delivery device according to claim 16, wherein the time varying electrical signal has an amplitude value in the range 100-200 mV.

23. A medication delivery device according to claim 16, wherein the time varying electrical signal has an amplitude of approximately 150 mV.

24. A medication delivery device according claim 13, wherein the needle mount is adapted to detachably retain the injection needle in a fixed position relative to the medication delivery device.

25. A medication delivery device according to claim 13, wherein the medication delivery device comprises a log for saving the position of an injection.

26. A medication delivery device according to claim 25, wherein the log is adapted to save the position of an injection with associated parameters, the associated parameters being one or more parameters selected from the group of time of injection, amount of injected medicament and type of medicament.

* * * * *